United States Patent
Dringenberg

(10) Patent No.: US 8,876,775 B2
(45) Date of Patent: Nov. 4, 2014

(54) NEEDLE SAFETY CAP

(76) Inventor: Steven A. Dringenberg, Camino, CA (US)

(*) Notice: Subject to any disclaimer, the term of this patent is extended or adjusted under 35 U.S.C. 154(b) by 793 days.

(21) Appl. No.: 12/618,977

(22) Filed: Nov. 16, 2009

(65) Prior Publication Data

US 2011/0118673 A1 May 19, 2011

(51) Int. Cl.
- *A61M 5/178* (2006.01)
- *A61B 17/34* (2006.01)
- *A61B 19/00* (2006.01)
- *A61M 5/32* (2006.01)

(52) U.S. Cl.
CPC ......... *A61B 17/3415* (2013.01); *A61B 17/3494* (2013.01); *A61B 2019/4805* (2013.01); *A61M 5/3213* (2013.01)
USPC ....... 604/164.08; 604/110; 604/192; 604/263

(58) Field of Classification Search
USPC ...................... 604/110, 164.08, 192, 198, 263
See application file for complete search history.

(56) References Cited

U.S. PATENT DOCUMENTS

| | | | |
|---|---|---|---|
| 4,757,827 A * | 7/1988 | Buchbinder et al. | 600/585 |
| 5,053,017 A * | 10/1991 | Chamuel | 604/192 |
| 5,201,721 A | 4/1993 | Lee et al. | |
| 5,232,454 A | 8/1993 | Hollister | |
| 5,688,241 A * | 11/1997 | Asbaghi | 604/110 |
| RE37,110 E | 3/2001 | Hollister | |
| 6,280,419 B1 * | 8/2001 | Vojtasek | 604/192 |
| 6,613,039 B1 | 9/2003 | Namba | |
| 6,652,490 B2 * | 11/2003 | Howell | 604/164.08 |
| 6,743,203 B1 * | 6/2004 | Pickhard | 604/139 |
| 6,986,759 B1 * | 1/2006 | Jeremijevic | 604/198 |
| 2004/0092891 A1 | 5/2004 | Spranza et al. | |
| 2008/0097343 A1 * | 4/2008 | Woehr | 604/263 |
| 2009/0163861 A1 * | 6/2009 | Carlyon | 604/110 |
| 2010/0137810 A1 | 6/2010 | Chandrasekaran et al. | |

FOREIGN PATENT DOCUMENTS

CA 2337557 9/2001

* cited by examiner

*Primary Examiner* — Emily Schmidt
(74) *Attorney, Agent, or Firm* — Renner Kenner Greive Bobak Taylor & Weber

(57) ABSTRACT

A safety cap for use with a needle, the cap including an opening in the cap adapted to receive a needle therein, a releasable lock mechanism disposed within the opening, and a permanent lock mechanism disposed within the opening. The safety cap may be provided on a needle, the releasable locking mechanism being actuated to release the needle from the cap. After use, the needle may be reinserted into the safety cap and permanently locked therein by the permanent locking mechanism, thereby providing for safe disposal of the used needle.

15 Claims, 10 Drawing Sheets

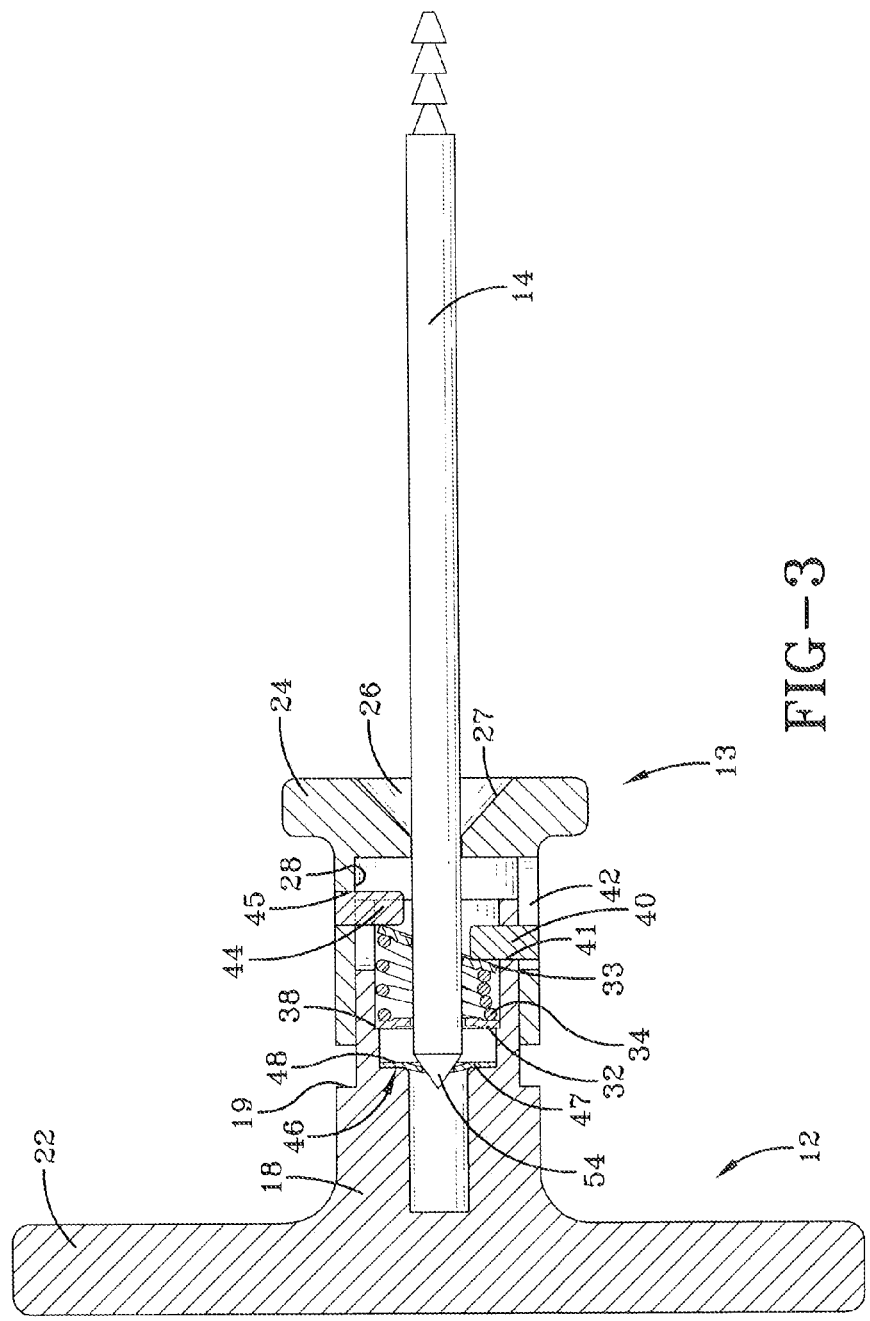

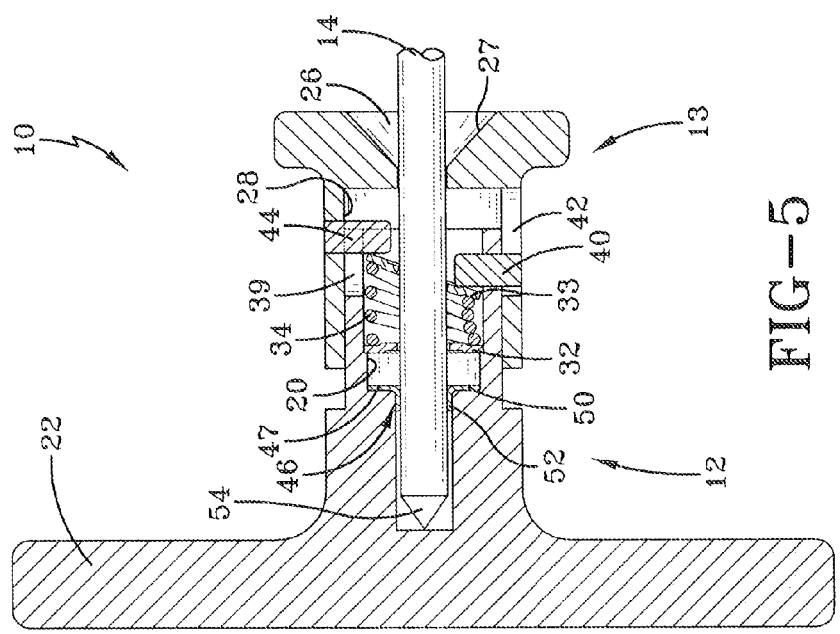
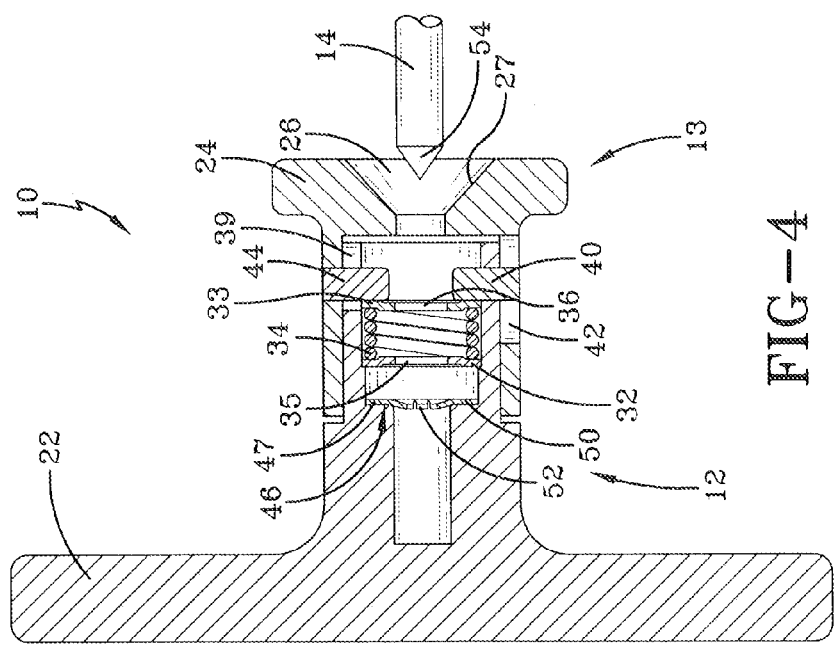

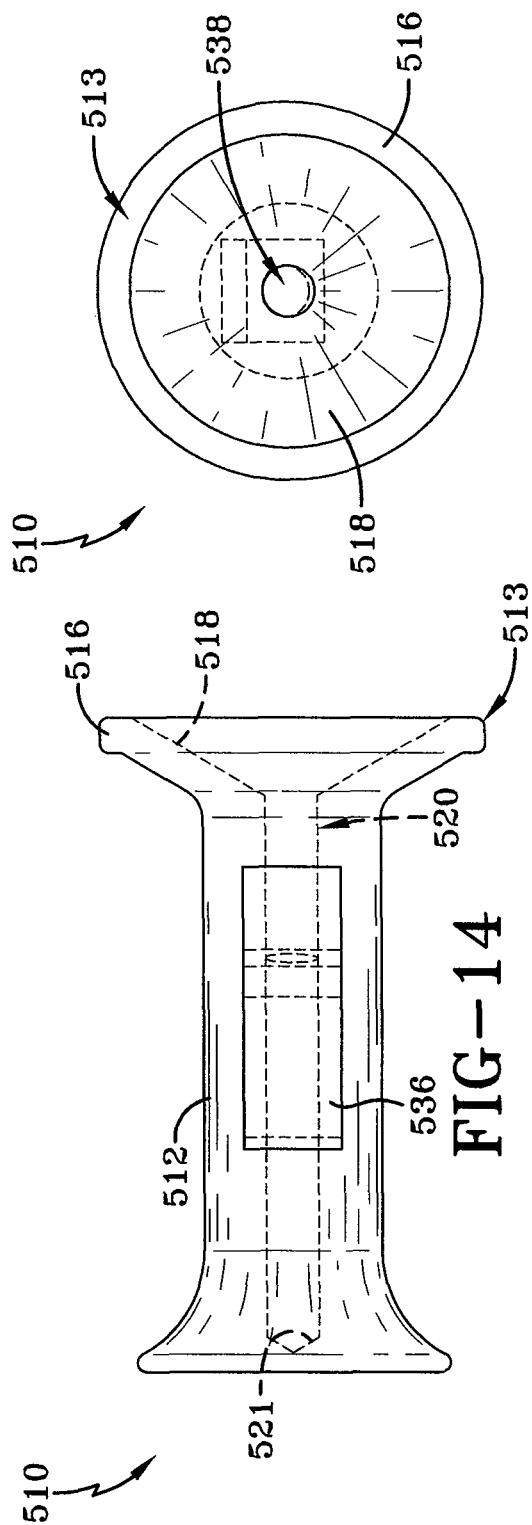

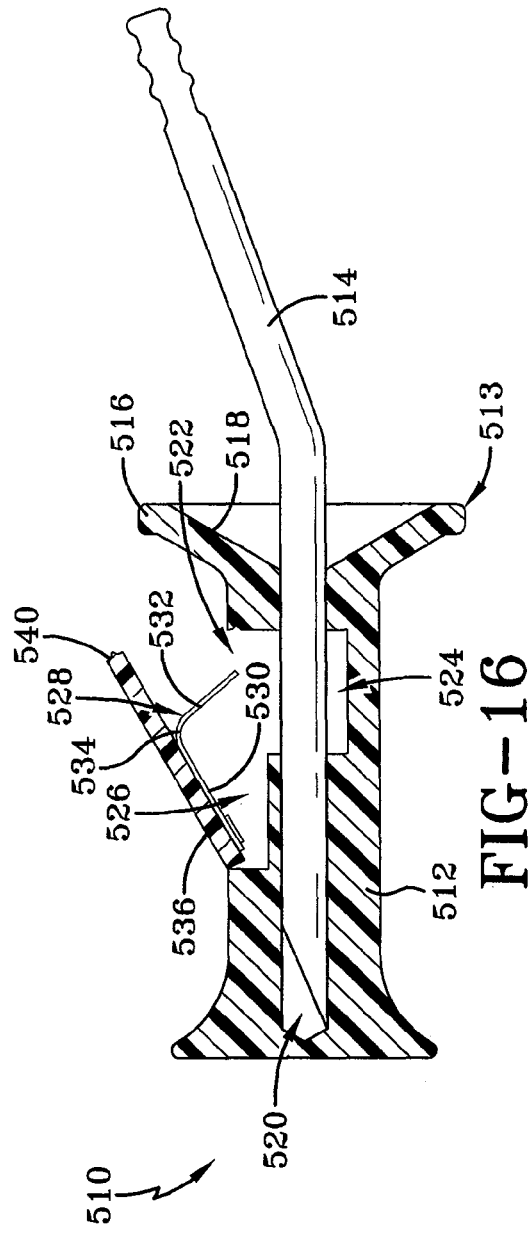
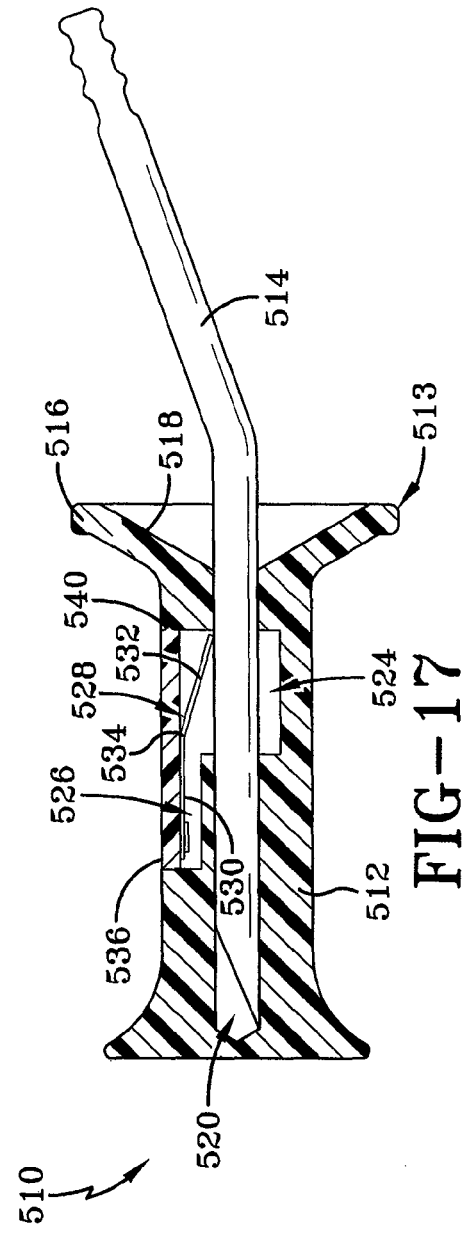

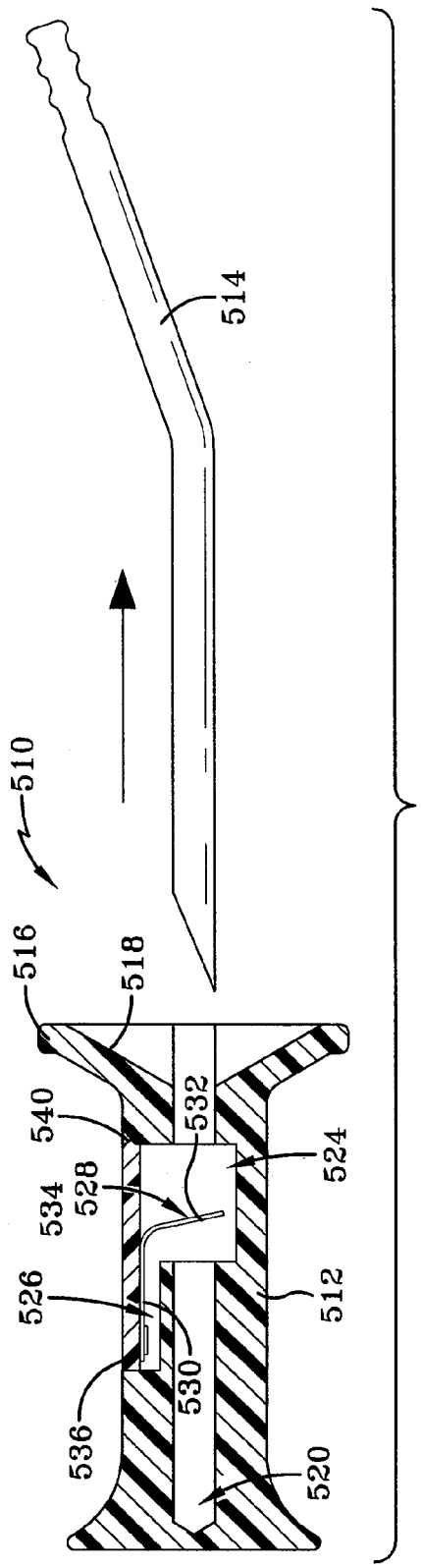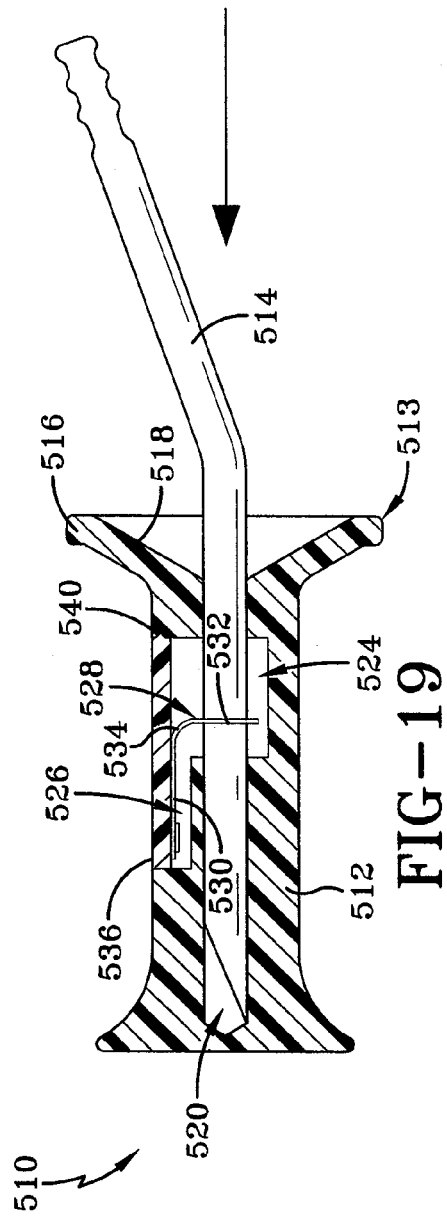
FIG-18
FIG-19

NEEDLE SAFETY CAP

FIELD OF THE INVENTION

Generally, the present invention relates to a safety cap for use on a pointed object. More particularly, the present invention relates to a safety cap for a needle, wherein the cap includes a releasable lock mechanism and a permanent lock mechanism and is adapted to cover the pointed end of the needle.

BACKGROUND OF THE INVENTION

A major concern for health care professionals, including doctors, physician assistants, nurses, and medical technicians, is their own personal safety while providing medical care to others. Often, these health care professionals are required to perform procedures on patients who have transmittable diseases and pathogens, such as HIV, Hepatitis B, Hepatitis C, staphylococcus and streptococcus bacteria, as well as others. Surgery, in particular, presents significant risks to doctors and nurses because they must use sharp instruments in confined spaces, with the instruments becoming covered in the patient's own blood, serum, bile, and pus. If a doctor or nurse were to stab or jab themselves with one of these sharp instruments they would be at significant risk of contracting whatever diseases or pathogens the patient was carrying.

One surgical device which is of particular concern, and which presents heightened risks, is a trocar. A trocar is an elongated, highly polished, spear-like instrument that is typically utilized to create stab wounds through a patient's soft tissue. The trocar usually has a tube or drain attached to one end, and a point on the other, so that the pointed end may be inserted into and advanced through the patient's soft tissue in order to create a passageway for the tube, which then acts as a drain for fluids within the body cavity where a surgical procedure is to be performed. A variety of designs for the sharp points on the trocar are available, some with sharp ridges to cut flesh and others with conical pointed ends.

The drain tube is cut from the trocar after the trocar has advanced through the patient's soft tissue to create an opening. The drain tube extends from the body, through the patient's soft tissue, and to a reservoir outside the body to collect fluids. Surgical drain tubes are used in a wide variety of surgical procedures, and are typically made from soft materials such as plastics and rubbers.

Trocars have conventionally been inserted by hand by a doctor or nurse wearing gloves. The trocar is usually inserted into the body cavity, forced through the patient's soft tissue by hand from within the cavity, and then grasped from the outside and advanced the remainder of the way through the tissue until only the hose is extending through the opening in the patient's soft tissue. Because the trocar is highly polished and the environment in which it is used contains various fluids, it is difficult for doctors and nurses to grasp the device to push or pull it through the patient's soft tissue. Furthermore, it is extremely dangerous to grasp the pointed end of the trocar when attempting to advance it through the patient. Difficulties encountered while using the trocar may also be dangerous to the patient because a slip or error while doing so could cause unnecessary harm to the patient. Another concern with trocar devices is their safe disposal after being used. Oftentimes, a trocar is covered in a patient's fluids after being inserted through the patient's soft tissue, and by virtue of its sharp pointed end continues to present a hazard when discarded. If improperly disposed of, trocars will be a danger to anyone who subsequently handles them or comes in contact with them.

Several devices have been developed to assist in the insertion of trocars during surgical procedures. These devices, disclosed in U.S. Pat. No. 6,613,039 and U.S. Patent Application No. 2004/0092891, include a holder mechanism for holding a trocar and a receiving mechanism for receiving the trocar. In use, the holder mechanism is positioned in or adjacent to the internal cavity within the patient and the receiving mechanism is positioned on the exterior of the patient to receive the trocar after it passes through the patient's soft tissue. These devices, while providing some safety advantages, are unnecessarily large and bulky, are awkward to use due to their size and shape, and require cleaning and sanitization between uses to prevent contamination from one patient to another.

Thus, it is believed that there is a need for an economical and easy to use safety device to assist health care professionals in using trocar devices, and other needles, while also protecting them from possible contamination due to pathogens carried by the patient.

SUMMARY OF THE INVENTION

Any one or more of the foregoing aspects of the present invention, together with the advantages thereof over known art relating to safety caps for pointed objects which will become apparent from the specification and drawings that follows, may be accomplished by the invention as hereinafter described and claimed.

In general, the present invention provides a safety cap for use with a needle that has a releasable locking mechanism and a permanent locking mechanism. One or more other aspects of the present invention may be achieved by a safety cap for use with a needle, the cap comprising a bore in the cap adapted to receive a needle therein, and a locking spring having a hole therethrough and adapted to flex between a first position and a second position. The spring is adapted to releasably secure a needle within the cap when in the second position and to permanently secure a needle within the cap when in the first position.

The same or one or more other aspects of the present invention may be achieved by a needle assembly including a needle having a pointed end, and a safety cap including a locking spring. The locking spring is adapted to releasably secure the pointed end of the needle within the cap prior to use of the needle and is adapted to permanently secure the pointed end of the needle in the safety cap after reinsertion of the needle into the safety cap.

BRIEF DESCRIPTION OF THE DRAWINGS

FIG. 3 is a sectional view of the needle safety cap assembly taken substantially along line 3-3 of FIG. 1 wherein the needle is in a releasably locked position.

FIG. 4 is a sectional view of the needle safety cap assembly of FIG. 3 in a released position.

FIG. 5 is a sectional view of the needle safety cap assembly of FIG. 3 in a permanently locked position.

FIG. 14 is a top view of a needle safety cap assembly according to the concepts of a sixth embodiment of the present invention.

FIG. 15 is a front view of the needle safety cap assembly of FIG. 14.

FIG. 16 is a sectional view of the needle safety cap assembly of FIG. 14, wherein the needle is positioned in the safety cap but is not yet locked therein.

FIG. 17 is a sectional view of the needle safety cap assembly of FIG. 14, wherein the needle is releasably locked in the safety cap.

FIG. 18 is a sectional view of the needle safety cap assembly of FIG. 14, wherein the needle has been removed from the safety cap.

FIG. 19 is a sectional view of the needle safety cap assembly of FIG. 14, wherein the needle is permanently locked within the safety cap.

DETAILED DESCRIPTION OF ILLUSTRATIVE EMBODIMENTS

Figure 1:
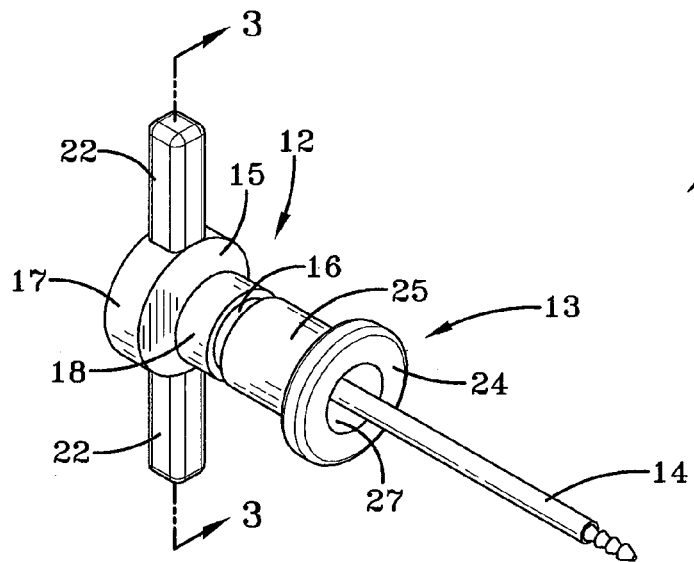
FIG. 1 is a perspective view of a needle safety cap assembly according to the concepts of a first embodiment of the present invention.

A first embodiment of the needle safety cap assembly according to the concepts of the present invention is shown in FIGS. 1-5 and is indicated generally by the numeral 10. Needle safety cap assembly 10 generally includes an adjustable body member, generally indicated by the numeral 12, and a needle-receiving sleeve, generally indicated by the numeral 13. In at least one embodiment, the sleeve 13 is slidably engaged to the body member 12, and together, the body member 12 and sleeve 13 operate to receive a needle 14 and either releasably lock or permanently lock the needle safety cap assembly 10 onto the pointed end of the needle 14. In one embodiment, the needle 14 may be released and physically separated from the needle safety cap assembly 10 while in use, but rejoined to the needle safety cap assembly 10 upon completion of its use as more specifically detailed below.

Figure 2:
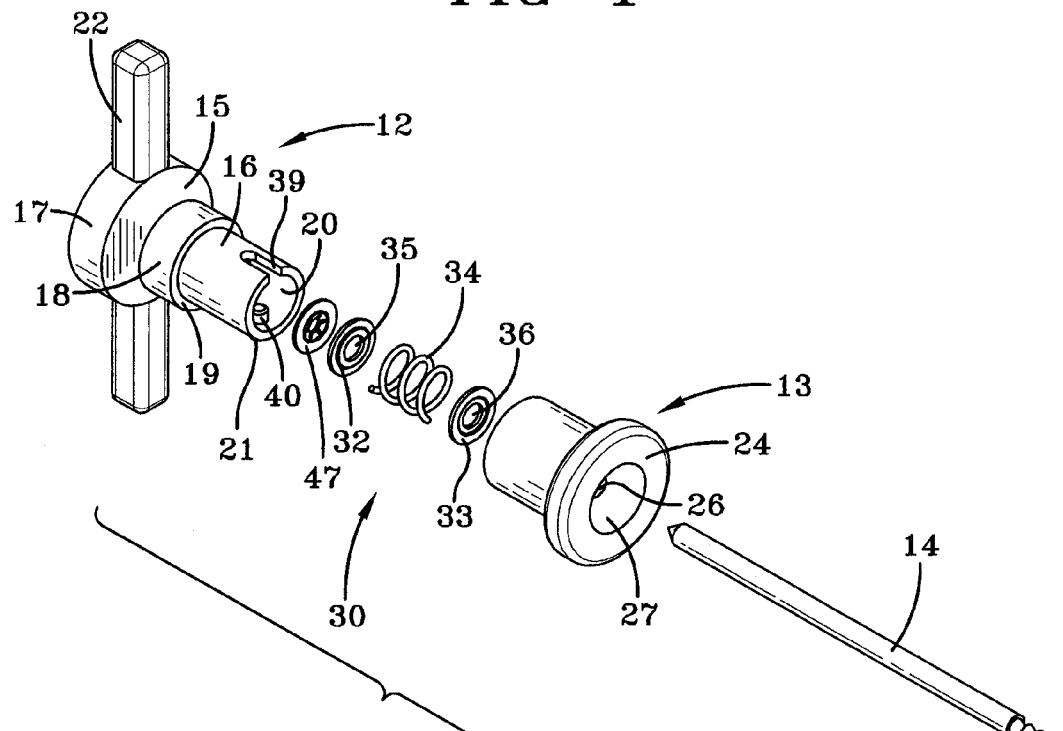
FIG. 2 is an exploded perspective view of the needle safety cap assembly of FIG. 1.

In at least one embodiment, the body member 12 of the needle safety cap assembly 10 is elongated and includes a body portion 15 and a neck 16 extending therefrom. Body portion 15 may have any shape or configuration known in the art, but should be adapted to be useful for its intended purpose. As shown in FIGS. 1-2, body portion 15 includes a generally cylindrical portion 17 with an extending flange 18 adapted to receive the neck 16. Neck 16 has a smaller cross-sectional profile than the flange 18 of body portion 15 and is separated therefrom by a shoulder 19 formed by the intersection of neck 16 and body portion 15. A bore 20 is defined by the inside diameter of a wall 21 of neck 16 and extends through neck 16 and at least partially through body member 12. Body member 12 may optionally include a handle or handles, such as arms 22 extending from body portion 15. In one embodiment, handle 22 may extend radially from body portion 15. In another embodiment, handle 22 may be releasable from body portion 15. Handle 22 may be of any size, shape or configuration known in the art but should be adapted to make holding and gripping the needle safety cap assembly 10 easier for a user. As shown in FIGS. 1 and 2, handle 22 includes a pair of arms extending from body member 12.

As shown in FIGS. 1 and 2, sleeve 13 of needle safety cap assembly 10 may be slidably positioned on neck 16 of body member 12. More particularly, in the embodiment illustrated, sleeve 13 is provided with a needle receiving portion 24 and a flange 25 extending therefrom. The receiving portion 24 may have any shape or configuration known in the art, but should be adapted to be useful for its intended purpose. The receiving portion 24 defines an opening 26 therein for receiving the needle 14. In one embodiment, the opening 26 is more particularly defined by a wall 27 that is tapered to facilitate insertion of a needle 14, as will be discussed in greater detail below. At its narrowest, opening 26 should be large enough in diameter to allow the needle 14 to easily be received therethrough.

In the embodiment shown, flange 25 is generally cylindrical in shape and defines an inner cavity 28 for receiving neck 16. Flange 25 may be provided in any shape known in the art, but should be of a size and shape that is complementary to neck 16 such that neck 16 is slidably received within flange 25. In an alternative embodiment, flange 25 may be smaller in diameter than neck 16 and, as such, may be slidably received within neck 16. As best seen in FIGS. 3-5, flange 25 has an inner diameter that is approximately equal to but slightly greater than the outer diameter of neck 16, thereby allowing flange 25 to be slidingly received on neck 16. Flange 25 is aligned coaxially on neck 16 such that bore 20, opening 26 and inner cavity 28 are coaxial with one another. Shoulder 19 may act as a stop in one direction to prevent further sliding of sleeve 13 in that direction.

As shown in FIGS. 2 and 3, a releasable locking mechanism, generally indicated by the numeral 30, is disposed within needle safety cap assembly 10. In the embodiment illustrated, releasable locking mechanism 30 includes a first annular washer 32, a second annular washer 33, and a spring 34. As with most washers, both first washer 32 and second washer 33 have an aperture 35 and 36 therethrough, respectively. Spring 34 has an outer diameter approximately equal to the outer diameter of washers 32 and 33 and is generally aligned with the washers 32, 33. As more particularly shown in FIG. 3, first washer 32 is received coaxially in bore 20 of neck 16 and is retained in place by a lip 38 within bore 20 where the inner diameter of bore 20 decreases in size. Spring 34 is aligned coaxially with first washer 32 and within bore 20 with one end of the elongated spring positioned adjacent to and in contact with first washer 32. Second washer 33 is positioned such that its center within aperture 36 lies on an axis with first washer 32 and spring 34 within bore 20 or inner cavity 28, and is adjacent to and in at least partial contact with an end of spring 34 opposite the first washer 32, but, as shall be described, second washer 33 is not necessarily coaxial with the spring 34 and first washer 32. Nevertheless, spring 34 is "sandwiched" between washers 32 and 33 within bore 20.

As best shown in FIG. 2, wall 21 of neck 16 of body member 12 is provided with a slot 39 extending longitudinally from the end of wall 21 distal to the body portion 15 for a distance less than the full length of neck 16. A first projection 40 is provided through a projection-receiving aperture 41 in neck 16 such that at least a portion of the projection extends into bore 20 diametrically opposite of slot 39. A portion of first projection 40 also extends outward from neck 16 and First projection 40 may be secured within neck 16 by any method known to those skilled in the art, such as, for example, by using a cylindrical rod press fit into the projection-receiving aperture 41 within neck 16, or, for example, by using a threaded screw to thread the screw into a threaded aperture 41 in neck 16. First project 40 is accessible from outside of sleeve 13 because sleeve 13 includes a slot 42 within flange 25. That is, flange 25 includes a slot 42 extending longitudinally for a distance less than the full length of flange 25.

A second projection 44 is provided through a second projection-receiving aperture 45 in sleeve 13 such that at least a portion of that protection extends within inner cavity 28 diametrically opposite of slot 42. This second projection 44 may be secured within sleeve 13 by any method known to those skilled in the art, such as, again, by using a cylindrical rod press fit into the second projection-receiving aperture 45 within flange 25, or, for example, by using a threaded screw to thread the screw into a threaded aperture 45 in flange 25.

Thus, when assembled, first projection 40 is received within slot 42 on sleeve 13, and second projection 44 is received in slot 39 in neck 16. The interaction of the projections and slots act to secure sleeve 13 to neck 16 while also controlling and restricting the movement of sleeve 13 relative to body member 12.

A permanent locking mechanism, generally denoted by the numeral 46, may also be provided within bore 20, and is generally distal from the needle receiving opening 26 of the safety cap assembly 10, as compared to the releasable locking mechanism 30. The permanent locking mechanism 46 may be adjacent to and in contact with a second lip 48 defined by another decrease in the diameter of bore 20, and therefore, may be coaxial with the first washer 32 and spring 34 of the releasable locking mechanism 30. It will be appreciated that permanent locking mechanism 46 may be any mechanism known to persons skilled in the art that is capable of permanently securing a narrow rod-like article, such as a needle, therein. In the embodiment of the invention shown in FIGS. 1-5, the permanent locking mechanism 46 is a lock washer 47, as is well known in the art. Lock washer 47 includes a solid outer annular portion 50 and inwardly extending teeth 52. Teeth 52 are capable of deflecting and when deflected act to secure a needle within safety cap 10, as will be discussed in greater detail below.

With reference now to FIG. 3, a needle 14 with a pointed end 54 is shown releasably secured within safety cap 10 by releasable locking mechanism 30. Needle 14 is positioned within apertures 35 and 36 of first and second washers 32 and 33, respectively, and within spring 34. In the unactuated state of FIG. 3 second washer 33 is biased by spring 34 such that it is not coaxial with the first washer 32 or spring 34. In this manner, second washer presses on first projection 40 of neck 16 and second projection 44 of sleeve 13. Second projection 44, and consequently sleeve 13, is pressed by spring 34 in the direction opposite of first washer 32 as far as allowed by slot 42. Due to the placement of first projection 40, which is closer to first washer 32 than second projection 44, second washer 33 is angled relative to first washer 32 when safety cap assembly 10 is in an unactuated state. The angle of second washer 33 effectively reduces the size of aperture 36, causing it to contact and engage needle 14 and prevent it from being pulled out of safety cap assembly 10. That is, the bias pressure of spring 34 that acts upon second washer 33, together with the fact that first and second projections 40 and 44 are not aligned opposite each other, causes the second washer 33 to turn at an angle and effectively hold the needle 14 in place within the safety cap assembly 10.

Based upon the embodiment shown in FIG. 3, needle 14 may be removed from safety cap assembly 10 as shown in FIG. 4. When sleeve 13 is pressed towards handle 22 of body member 12 (or vice versa), second projection 44 slides within slot 39 and first projection 40 slides within slot 42, until the first and second projections 40 and 44 are substantially aligned with each other. This movement of the first and second projections 40, 44 allows second washer 33 to turn from its irregular angle so as to be aligned and substantially coaxial with the first washer 32. In other words, pressing the sleeve 13 and body member 12 together will act to compress the spring 34 and bring the projections 40, 44 into alignment. When safety cap assembly 10 is fully compressed as far as first projection 40 and slot 42 will permit, second washer 33 is substantially parallel and coaxial to first washer 32, thereby effectively increasing the size of aperture 36 of the second washer 33. Thus, the compressing of safety cap assembly 10 by pressing sleeve 13 and body member 12 together actuates release lock mechanism 30 to release needle 14 and allow it to be pulled out. When needle 14 is removed and sleeve 13 is released, safety cap assembly 10 returns to an unactuated state by virtue of the biasing force of spring 34. Needle 14 may be provided to medical personal having safety cap assembly 10 already positioned thereon, cap assembly 10 being removed from needle 14 prior to its use.

With reference to FIG. 5, needle 14 is shown permanently secured within safety cap assembly 10. After needle 14 has been used it is reinserted into safety cap assembly 10 so that pointed end 54 is covered and poses no danger to the surgeons or the patient. Needle 14 is pushed into cap assembly 10 through needle receiving opening 26 and into inner cavity 28 and, further, through bore 20 until it passes through permanent lock mechanism 46, which in this case is a lock washer 47. As needle 14 passes through lock washer 47, teeth 52 deflect in the direction of travel and then engage needle 14 to prevent movement in the opposite direction. In this way, needle 14 is permanently secured within safety cap assembly 10 once the needle is fully inserted so that it passes through lock washer 47. In cases where needle 14 is a trocar, once needle 14 is permanently secured in safety cap assembly 10 handle 22 may be used to assist in advancing it the rest of the way through the patient's soft tissue. Needle 14 may then be disposed of with safety cap assembly 10 permanently locked thereon, preventing anyone from being exposed to pointed end 54, which is now covered in the patient's fluids.

Although the embodiment shown in FIGS. 1-5 is one embodiment for a safety cap assembly 10 of the present invention, it will be appreciated that other embodiments may exist without detracting from the scope of the present invention. Thus, it will be understand that other embodiments exist and, in particular, the releasable locking mechanism and the permanent locking mechanisms disclosed above are not viable mechanism embodiments that can be used in the present invention to provide safe disposal of a needle.

Figure 6:
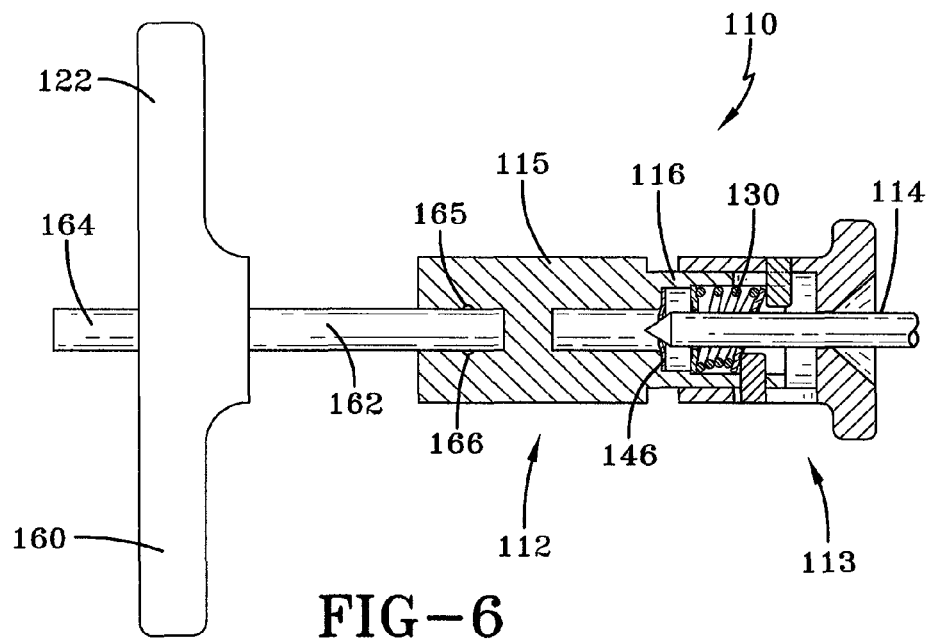
FIG. 6 is sectional view of a needle safety cap assembly having a removable handle according to the concepts of a second embodiment of the present invention.
Figure 7:
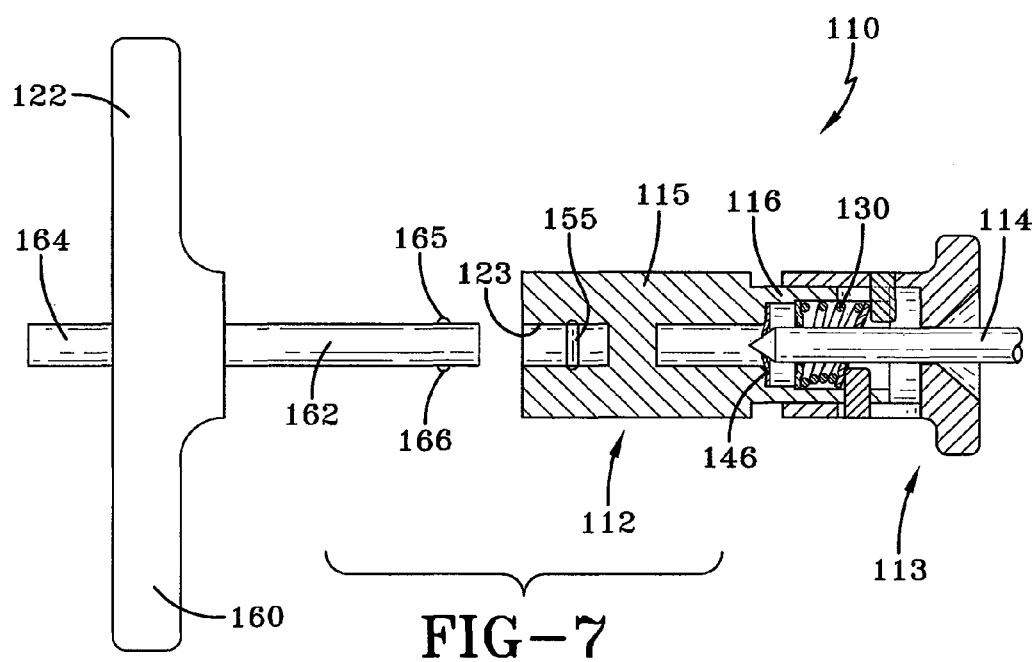
FIG. 7 is a sectional view of the needle safety cap assembly of FIG. 6 with the handle removed.

FIGS. 6 and 7 depict an alternative embodiment of the safety cap assembly of the present invention, generally referred to by the numeral 110, that is identical to the first embodiment discussed above except for an alternate handle design. Safety cap assembly 110 includes a body member 112 with body portion 115 and a neck 116, and a sleeve 113 slidably positioned on the neck 116. Safety cap assembly 110 also includes a releasable locking mechanism 130 and a permanent locking mechanism 146 adapted to secure the cap to a needle 114. Unlike in the first embodiment of the invention, body member 112 also includes a handle bore 123 extending partially therethrough in an end opposite sleeve 113. Handle bore 123 includes an annular recess 155 therein for receiving knobs of a handle post as described herein.

A removable handle 122 is provided having a gripping portion 160, a post 162, and a pushbutton 164. Post 162 may be secured within an aperture (not shown) in gripping portion 160 by any method known to those skilled in the art. Post 162 includes a pair of depressible knobs 165 and 166 which are biased outwardly from post 162, but which may retreat into the post 162 when pushbutton 164 is pressed and a force acts upon them. When post 162 and knobs 165 and 166 are inserted into handle bore 123, knobs 165, 166 are received in annular recess 155 to prevent removable handle 122 from being removed from handle bore 123, as is well known in the art. Although a specific mechanism for securing handle 122 in body member 112 of safety cap assembly 110 is described and shown in FIGS. 6 and 7, it should be appreciated that any known mechanism for releasably securing a handle to the safety cap may be used without deviating from the scope of the present invention. Removable handle 122 may be reused with a plurality of safety caps 110, thereby reducing manufacturing costs and preventing material waste.

Figure 8:
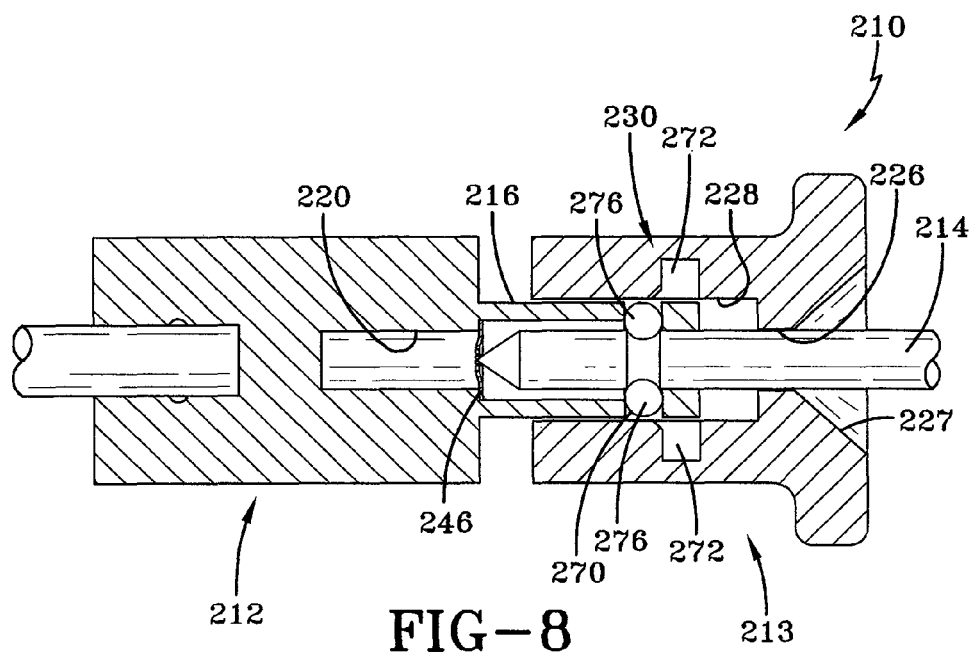
FIG. 8 is a sectional view of a needle safety cap assembly according to the concepts of a third embodiment of the present invention wherein the needle is in a releasably locked position.
Figure 9:
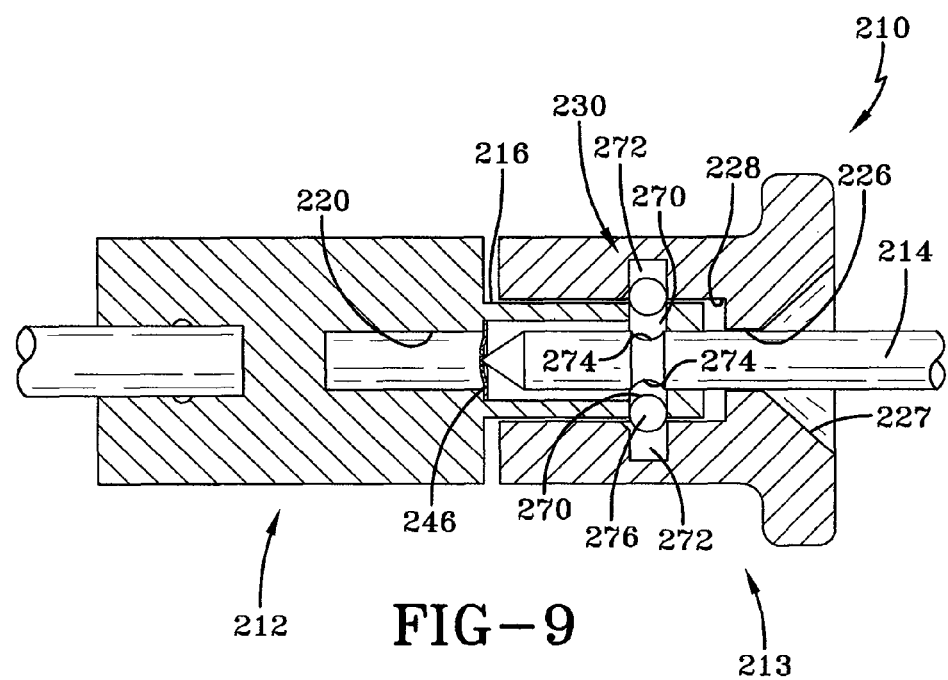
FIG. 9 is a sectional view of the needle safety cap assembly of FIG. 8, wherein the safety cap is in a released position.

FIGS. 8 and 9 show a third embodiment of the safety cap assembly of the present invention, this one being generally indicated by the numeral 210 and including an alternate releasable locking mechanism. Safety cap assembly 210 includes a body member 212 with a neck 216, and a sleeve 213 slidably positioned on neck 216. A bore 220 is provided through neck 216 and into body member 212. Sleeve 213 defines an inner cavity 228 and includes a first opening 226 opposite body member 212. The inner cavity 228 receives neck 216 of body member 212. First opening 226 may have a tapered surface 227 to facilitate receipt of a needle. Openings 220 and inner cavity 228 are elongated and positioned coaxially with bore 220 when sleeve 213 is positioned on neck 216, so that cap assembly 210 is adapted to receive a needle 214 therein. Safety cap assembly 210 includes a releasable locking mechanism 230 and a permanent locking mechanism 246.

In this embodiment, neck 216 of body member 212 is provided with a pair of ball pockets 270 that provide an opening from the exterior of neck 216 into bore 220 within neck 216. Pockets 270 may be cylindrical in shape, and may be positioned so that they have a cross-sectional profile substantially perpendicular to the cross-sectional profile of bore 220. Sleeve 213 is provided with an annular recess 272 extending from internal cavity 228 into sleeve 213. Annular recess 272 may have a width approximately equal to the diameter of pockets 270. Needle 214 is provided with an annular depression 274 therein, the depression having a concave radius. A ball 276 is provided within each ball pocket 270. Balls 276 have a radius approximately equal to but less than the radiuses of ball pockets 270 and annular depression 274, and the width of annular recess 272. Balls 276 may be retained within ball pockets 270 and prevented from falling into bore 220 by any method known to those skilled in the art, such as, for example, by providing a flange or lip extending into pockets 270 adjacent bore 220 so that balls 276 are prevented from escaping pockets 270.

When safety cap assembly 210 is in an unactuated position, or an extended position as seen in FIG. 8, annular recess 272 and ball pockets 270 are not aligned, so balls 276 are retained within pockets 270 and protrude slightly into bore 220. If needle 214 is positioned therein with annular depression 274 aligned with pockets 270, balls 276 will be received in depression 274. Needle 214 cannot be removed from safety cap assembly 210 while balls 276 are received in depression 274. When sleeve 213 is pressed toward body member 212 on neck 216, as seen in FIG. 9, annular recess 272 moves into alignment with ball pockets 270, allowing balls 276 to move out of and away from annular depression 274. Needle 214 may then be removed from safety cap assembly 210 before allowing sleeve 213 to return to its unactuated state. It may also be necessary to press sleeve 213 toward body member 212, thereby aligning annular recess 272 with ball pockets 270, when inserting needle 214 into safety cap assembly 210 through opening 226.

Figure 10:
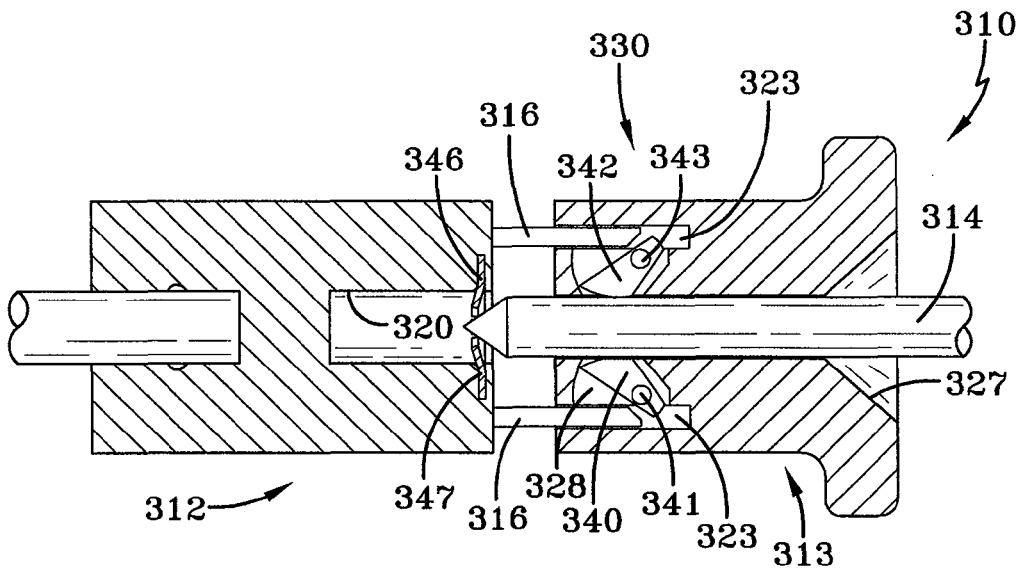
FIG. 10 is a sectional view of a needle safety cap assembly according to the concepts of a fourth embodiment of the present invention wherein the needle assembly is in a releasably locked position.
Figure 11:
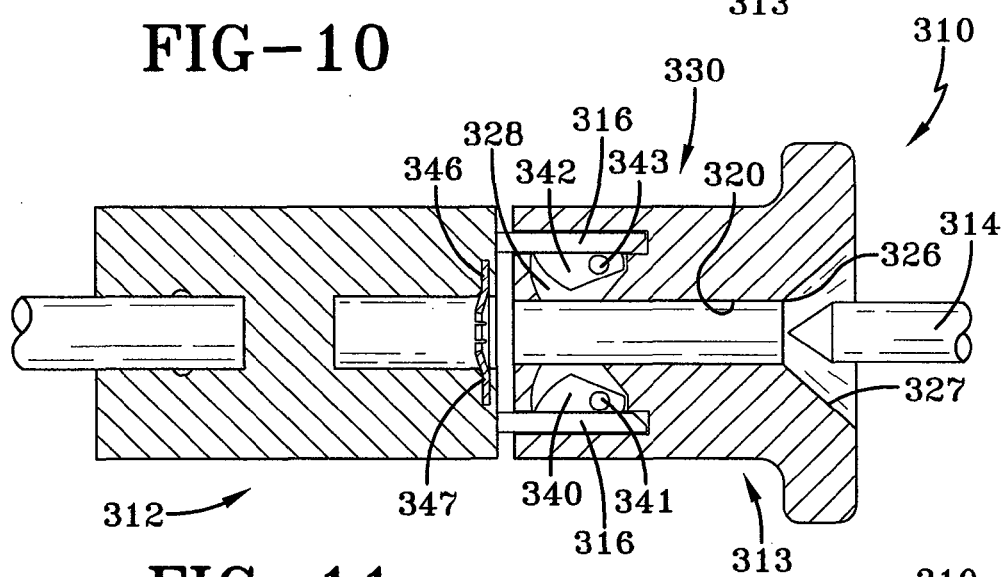
FIG. 11 is a sectional view of the needle safety cap assembly of FIG. 9 in a released position.
Figure 12:
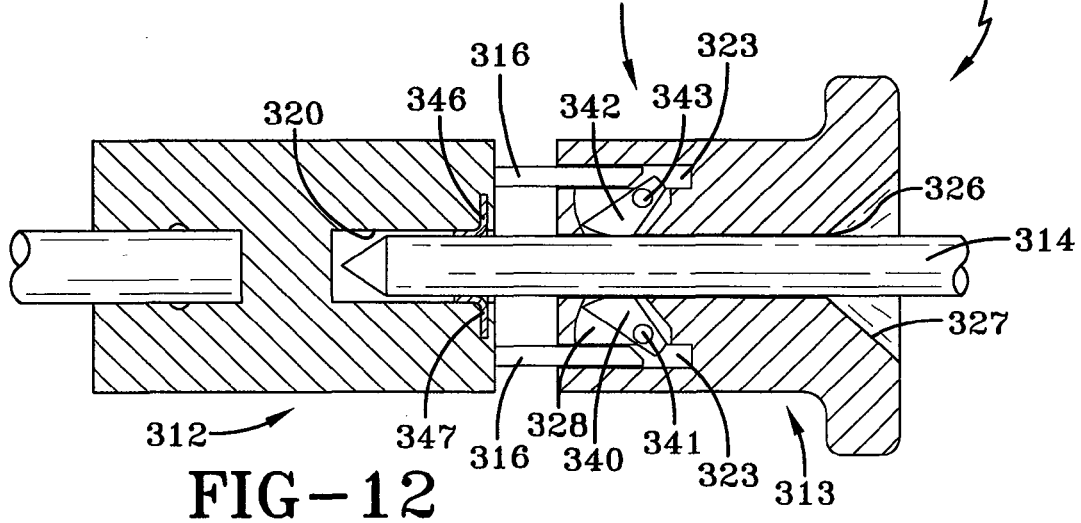
FIG. 12 is a sectional view of the needle safety cap assembly of FIG. 9 in a permanently locked position.

A fourth embodiment of the safety cap assembly according to the concepts of the present invention is shown in FIGS. 10-12, and is indicated generally by the numeral 310. Safety cap assembly 310 is similar to safety cap assembly 10 of the first embodiment, and includes a body member 312. However, instead of a neck, the safety cap assembly 310 includes a pair of posts 316 extending from body member 312, and a sleeve 313 with a pair of holes 323 slidably positioned on posts 316. A bore 320 passes through sleeve 313 and into body member 312, with an opening 320 on an end of sleeve 313 opposite body member 312. Opening 320 may have a tapered surface 327 to facilitate insertion of a needle 314. A permanent locking mechanism 346, such as a lock washer 347, like that disclosed in the first embodiment of the invention shown in FIGS. 1-5, is positioned within bore 320 in body member 312.

A releasable locking mechanism 330 is provided in sleeve 313. Releasable locking mechanism 330 includes a pair of pivoting arms 340, 342 positioned on pivot pins 341, 343, respectively. Arms 340, 342 are provided in an internal cavity 328 within sleeve 313 that provides space to allow arms 340, 342 to rotate about pivot pins 341, 343, respectively. Internal cavity 328 is partially open to holes 323 and to bore 320 such that a portion of arms 340, 342 can extend into holes 323, and an opposite portion can extend into bore 320. When needle 314 is inserted into bore 320 through opening 326, arms 340, 342 are forced to rotate in the direction of insertion when contacted by needle 314. If needle 314 is pulled in the opposite direction to be removed, arms 340, 342 engage and grab needle 314 and prevent its removal, as best seen in FIG. 10. To release needle 314, sleeve 313 is moved toward body member 312 on posts 316, as seen in FIG. 11, causing posts 316 to contact arms 340, 342. When arms 340, 342 are contacted by posts 316 moving into holes 323, they rotate away from needle 314 freeing it to be pulled out of bore 320. After needle 314 has been used it may be reinserted fully into safety cap assembly 310, thereby permanently securing it within safety cap 310 by virtue of permanent locking mechanism 346 as seen in FIG. 12. Permanent locking mechanism 346 is not unlike the locking mechanism presented in the first embodiment of this invention.

Figure 13:
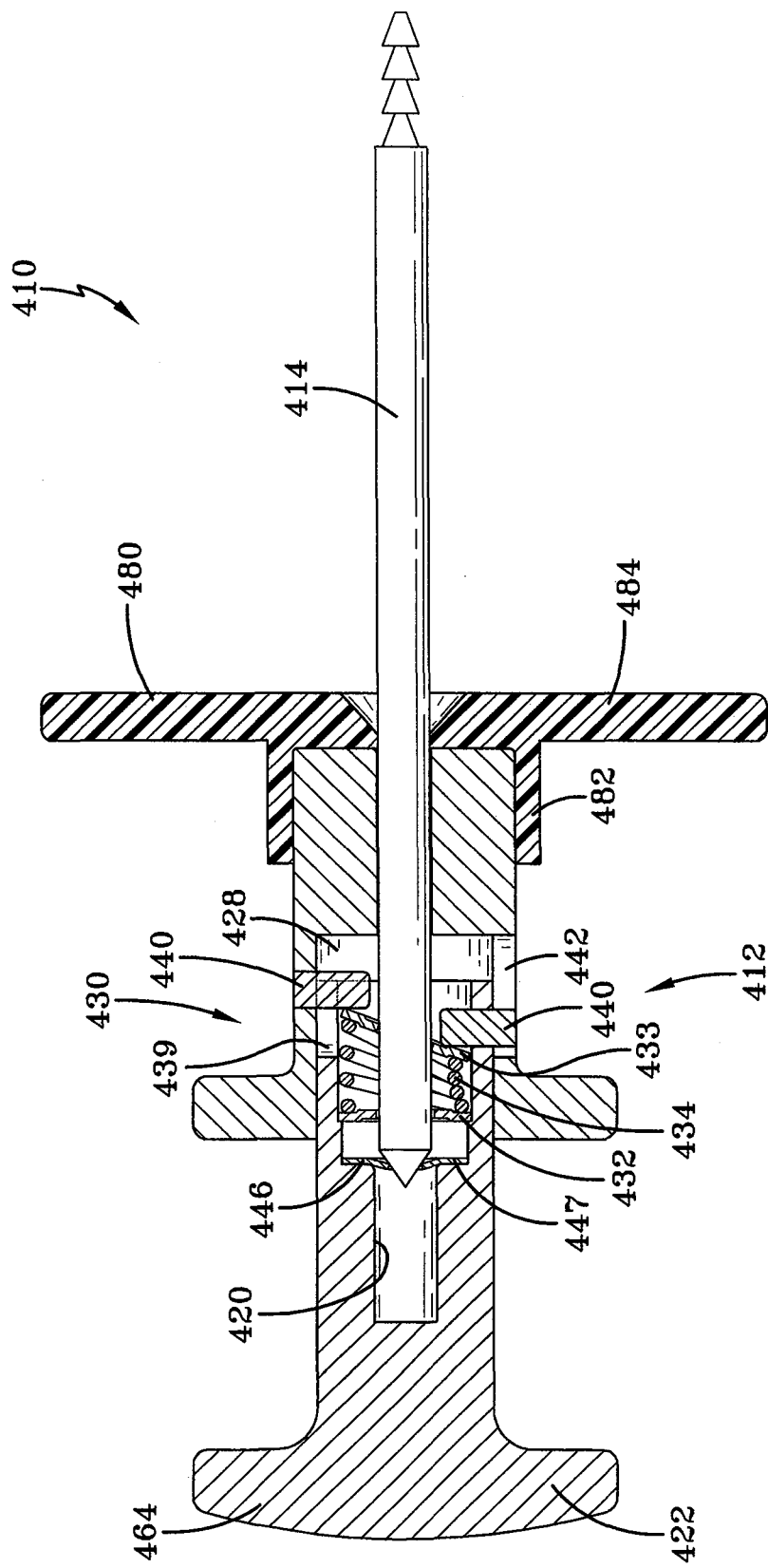
FIG. 13 is a sectional view of a needle safety cap assembly according to the concepts of a fifth embodiment of the present invention, wherein the needle is in a releasably locked position.

A fifth alternate embodiment of a safety cap assembly according to the concepts of the present invention is shown in FIG. 13 and is indicated generally by the numeral 410. Safety cap assembly 410 includes a body member 412 having a finger shield 480 on one end and an internal cavity 428 in an end opposite finger shield 480. Safety cap assembly 410 also includes a pushbutton 464 slidably received within cavity 428. A bore 420 extends through finger shield 480, body member 412 and partially through pushbutton 464, and is adapted to receive a needle 414. Finger shield 480 includes an annular flange 482 that fits around body member 412 and a shield plate 484 that extends radially from body member 412.

Safety cap assembly 410, like the other embodiments disclosed herein, includes a releasable locking mechanism 430 and a permanent locking mechanism 446. In the embodiment shown in FIG. 13, permanent locking mechanism 446 is a lock washer 447 and is identical to that disclosed in the first embodiment and shown in FIGS. 1-5, and releasable locking mechanism 430 is substantially the same as that described herein and shown in FIGS. 1-5. Releasable locking mechanism 430 includes a first projection 440, a second projection 444, a first slot 439 and a second slot 442 that interrelate and operate as in the first embodiment. Releasable locking mechanism 430 also includes a first washer 432, a second washer 433, and a spring 434 as previously described.

Pushbutton 464 includes a handle portion 422, which may be designed and shaped to fit comfortably in the palm of a user's hand. Safety cap assembly 410 comes releasably locked on needle 414. To release needle 414 for use, pushbutton 464 is pressed into internal cavity 428, thereby causing second projection 444 to move into axial alignment with first projection 440, causing second washer 433 to pivot and release needle 414. After needle 414 has been used, safety cap assembly 410 is placed over it with finger shield 480 facing the pointed end of the needle and protecting the user from being jabbed or cut. Finger shield 480 may optionally be made from a clear material, such as, for example, a clear plastic, so that a user of safety cap 410 can see through shield 480 to allow for easier insertion of needle 414 in safety cap assembly 410. Needle 414 is then pressed fully into bore 420 and through lock washer 447, permanently securing safety cap assembly 410 on needle 414, and, in the case of a trocar, allowing a user to pull on handle portion 422 to advance needle 414 the rest of the way through the patient.

Yet another embodiment of the safety cap assembly is shown in FIGS. 14-19 and is indicated generally by the numeral 510. Safety cap assembly 510 includes a body 512 that is generally cylindrical in shape. It should be appreciated, however, that body 512 may be provided in alternative shapes without deviating from the scope of the invention. Body 512 includes a receiving end 513 where a flange 516 extends outwardly therefrom. As shown in the drawings, flange 516 may include a generally tapered outer surface forming a generally conical protrusion from body 512. The interior of receiving end 513 includes a tapered wall 518 surrounding the opening of a bore 520 through body 512. Tapered wall 518 helps to funnel a needle 514 (FIGS. 16-19) into bore 520, which extends through body 512 and terminates at an end wall 521. Bore 520 is positioned concentrically within safety cap 510.

Body 512 also includes an inner chamber 522 around a section of bore 520. Inner chamber 522 includes a main chamber 524 that extends radially outward from bore 520 and a secondary chamber 526 that extends from and is connected to a portion of main chamber 524 and is oriented generally parallel with bore 520, as shown in FIGS. 16-19. A spring 528 is positioned within inner chamber 522 and is adapted to act as a locking mechanism. Spring 528 includes an anchor portion 530 and a locking portion 532 that is connected to the anchor portion 530 at an elbow 534.

As will be appreciated by those skilled in the art, spring 528 is provided in the form of a small strip of metal having high yield strength, and therefore possessing a tendency to return to its static position. As such, when spring 528 is forced to bend at elbow 534 in either direction it will, in response, exert a force in the opposing direction due to the tendency to return to the static position. Anchor portion 530 and locking portion 532 are oriented at an angle relative to one another by virtue of elbow 534. In one or more embodiments, anchor portion 530 and locking portion 532 are positioned at an angle of between approximately 95° and 140° relative to one another. Anchor portion 530 of spring 528 is secured to an outer wall of inner chamber 522 and extends between main chamber 524 and secondary chamber 526. Locking portion 532 extends from elbow 534 toward bore 520 and receiving end 513, thereby obstructing bore 520 when spring 528 is in its static position. Locking portion 532 of spring 528 includes a hole 538 therethrough. Hole 538 is generally aligned with bore 520 when spring 528 is in a static position.

A pivoting flap 536 is provided in body 512 of safety cap 510 that provides access to inner chamber 522. Flap 536 forms a portion of the outer wall of both main chamber 524 and secondary chamber 526, and anchor portion 530 of spring 528 is secured to the inner surface of flap 536. Anchor portion 530 may be secured to flap 536 by any method known to those skilled in the art, including by adhesives or mechanical fasteners. Flap 536 includes a lock 540 that prevents the flap from being reopened after it has been secured closed for the first time. In the embodiment depicted in the drawings, lock 540 is simply a tongue and groove type lock, as is well known in the art. It should be appreciated, however, that any lock known to those skilled in the art and suitable for the intended purpose may be used.

Referring now to FIGS. 16-19, the operation of safety cap 510 will be described. After manufacturing and before packing and shipping the product to a customer, flap 536 is in an open position, and spring 528 is partially exposed, as shown in FIG. 16. Needle 514, or any needle, is inserted through receiving end 513 of body 512 so that it is positioned within bore 520. Once needle 514 has been inserted into safety cap 510, flap 536 is closed, causing spring 528 to engage needle 514 and to bend at elbow 534, thereby applying pressure on needle 514, as shown in FIG. 17. When flange 536 is closed, lock 540 permanently secures flap 540 to body 512.

When needle 514 is first removed from safety cap 510 to be used, spring 528 returns to its static position and obstructs bore 520, as shown in FIG. 18. After needle 514 has been used, or is otherwise ready to be disposed of, it may be reinserted into bore 520 of safety cap 510. When needle 514 engages locking portion 532 of spring 528 as it is reinserted into bore 520 it causes spring 528 to bend at elbow 534 until locking portion 532 is generally perpendicular to anchor portion 530. When locking portion 532 is in the generally perpendicular position, hole 538 is substantially aligned with bore 520 and allows needle 514 to pass therethrough until it is fully inserted into safety cap 510, as shown in FIG. 19. Needle 514 is, at this point, permanently secured in safety cap 510 and can be safely disposed of. If an attempt is made to remove needle 514 from safety cap 510, the movement of needle 514 in the removal direction will cause locking portion 532 of spring 528 to move therewith, thereby causing the hole 538 to become un-aligned with bore 520. When the hole 538 is not substantially aligned with bore 520 it will bind or catch on the outer surface of needle 514 and prevent movement of the needle relative to the hole. An increased removal force acting on needle 514 will only cause an increased binding force on the needle by hole 538 that will prevent removal.

Although the present invention has been described in considerable detail with reference to certain embodiments, other embodiments are possible. Therefore, the spirit and scope of the appended claims should not be limited to the description of the embodiments contained herein.

What is claimed is:

1. A safety cap for use with a trocar, the cap comprising:
a bore defining a path for a trocar and adapted to receive a pointed tip of the trocar therein, said bore having an open end and a closed end for containing the trocar, and
a locking spring formed from a single flat strip of metal bent at an elbow said strip of metal having a circular hole therethrough which is spaced from a proximal end of the flat strip of metal relative to the open end of said bore, the proximal end of the locking spring adapted to flex at the elbow between a first position and a second position, the locking spring being adapted to releasably secure the trocar within the cap when in the first position to resist movement of the trocar away from the closed end of the bore absent an external force acting on the trocar, wherein the locking spring and the circular hole are not disposed within the path for the trocar when the locking spring is in the first position, and to permanently secure the trocar within the cap when in the second position to prevent any substantial movement of the trocar away from the closed end, and wherein the circular hole is disposed within and aligned with the path for the trocar when the locking spring is in the second position.

2. The safety cap of claim 1, wherein the locking spring includes an anchor portion, located at a distal end of the locking spring, and a locking portion, located at the proximal end of the locking spring, connected at the elbow and extending from one another at an angle, the locking portion having the hole therethrough.

3. The safety cap of claim 2, wherein the anchor portion and the locking portion extend from one another at an angle of between approximately 95° and 140°.

4. The safety cap of claim 1, further comprising an inner chamber within the cap and surrounding a portion of the bore.

5. The safety cap of claim 4, further comprising a pivoting flap that forms part of an outer wall of the inner chamber and provides access to the inner chamber from the exterior of the cap.

6. The safety cap of claim 5, wherein said locking spring is secured to an interior of the pivoting flap.

7. The safety cap of claim 6, wherein the locking spring includes an anchor portion and a locking portion extending from one another at an angle and connected at an elbow, the anchor portion being secured to the flap.

8. A trocar assembly comprising: a trocar having a pointed end, and a safety cap including a bore defining a path for the trocar and a locking spring having a circular hole therein which is spaced from a proximal end of the locking spring, said locking spring adapted to releasably secure the pointed end of the trocar within the bore of the safety cap when in a first position prior to use of the trocar, such that the circular hole and the locking spring are proximate to the bore but not disposed within the path of the trocar, and said locking spring adapted to permanently secure the pointed end of the trocar in the bore of the safety cap when the locking spring is in a second position after reinsertion of the trocar into the safety cap, removal of said safety cap from said trocar allowing said locking spring to move from said first position to said second position, said circular hole of said locking spring being positioned within and aligned with the path for the trocar in said safety cap having a closed end for containing the trocar and an open end.

9. The trocar assembly of claim 8, wherein the safety cap includes an inner chamber surrounding a portion of the bore.

10. The trocar assembly of claim 9, wherein the locking spring is made of a strip of metal.

11. The trocar assembly of claim 9, wherein the locking spring includes an anchor portion, located at a distal end of the locking spring, and a locking portion, located at the proximal end of the locking spring, extending from the anchor portion at an angle.

12. The trocar assembly of claim 11, wherein the locking portion extends from the anchor portion at an angle of between approximately 95° and 140°.

13. The trocar assembly of claim 11, wherein the anchor portion is secured to an outer wall of the inner chamber.

14. The trocar assembly of claim 9, further comprising a pivoting flap that forms part of the outer wall of the inner chamber.

15. A method of advancing a trocar through the body of a patient, the method comprising: permanently securing a safety cap to the trocar once the trocar has already been inserted into the patient, the safety cap comprising of a body member adapted to advance the trocar through the patient; a bore defining a path for the trocar and adapted to receive a pointed tip of the trocar therein, said bore having an open end and a closed end for containing the trocar; and a locking spring formed from a single flat strip of metal bent at an elbow, said strip of metal having a circular hole therethrough which is spaced from a proximal end of the flat strip of metal, the proximal end of the locking spring adapted to flex at the elbow between a first position and a second position, the locking spring being adapted to releasably secure the trocar within the cap when in the first position to resist movement of the trocar away from the closed end of the bore absent an external force acting on the trocar, wherein the locking spring and the circular hole are not disposed within the path for the trocar when the locking spring is in the first position, and to permanently secure the trocar within the cap when in the second position to prevent any substantial movement of the trocar away from the closed end, and wherein the circular hole is disposed within and aligned with the path for the trocar when the locking spring is in the second position.

* * * * *